United States Patent
Mori

(10) Patent No.: US 7,700,648 B2
(45) Date of Patent: Apr. 20, 2010

(54) ESTER COMPOUND AND ITS USE

(75) Inventor: Tatsuya Mori, Toyonaka (JP)

(73) Assignee: Sumitomo Chemical Company Limited, Tokyo (JP)

(*) Notice: Subject to any disclaimer, the term of this patent is extended or adjusted under 35 U.S.C. 154(b) by 767 days.

(21) Appl. No.: 10/598,126

(22) PCT Filed: Feb. 8, 2005

(86) PCT No.: PCT/JP2005/002198

§ 371 (c)(1),
(2), (4) Date: Aug. 18, 2006

(87) PCT Pub. No.: WO2005/082877

PCT Pub. Date: Sep. 9, 2005

(65) Prior Publication Data

US 2008/0161390 A1   Jul. 3, 2008

(30) Foreign Application Priority Data

Feb. 27, 2004   (JP)   .............................. 2004-053336

(51) Int. Cl.
*A01N 43/08*   (2006.01)
*C07D 307/45*   (2006.01)

(52) U.S. Cl. ...................................... 514/471; 549/496
(58) Field of Classification Search ................ 514/461, 514/471; 549/500, 501, 502, 496
See application file for complete search history.

(56) References Cited

OTHER PUBLICATIONS

Elliott et al., Pesticide Science (1976), 7(5), 499-502 (Abstract).*
Elliott et al, Journal of the Chemical Society, Perkin Transactions, Organic and Bio-Organic Chemistry (1974), (21), 2470-4.*
"Pest", Encyclopaedia Britannica, 2008.*
Michael Elliott, et al. "Insecticidal Activity of the Pyrethrin and Related Compounds X. 5-Benzyl-3-furylmethyl 2,2-dimethylcyclopropanecarboxylates with ethylenic substituents at position 3 on the cyclopropane ring", Pestic. Sci. 1976, 7. 499-502.

* cited by examiner

Primary Examiner—Bernard Dentz
Assistant Examiner—David E Gallis
(74) Attorney, Agent, or Firm—Panitch Schwarze Belisario & Nadel LLP

(57) ABSTRACT

(5-Benzyl-3-furyl)methyl 2,2-dimethyl-3-((E)-2-cayano-3-methoxy-3-oxo-1-propenyl)cyclopropanecarboxylate has an excellent pesticidal activity, and a pesticidal composition comprising it as an active ingredient is useful for controlling pests.

8 Claims, No Drawings

ESTER COMPOUND AND ITS USE

CROSS-REFERENCE TO RELATED APPLICATIONS

This application is a Section 371 of International Application No. PCT/JP2005/002198, filed Feb. 8, 2005, which was published in the English language on Sep. 9, 2005 under International Publication No. WO 2005/082877 A1 and the disclosure of which is incorporated herein by reference.

FIELD OF THE INVENTION

The present invention relates to an ester compound and its use for pesticide.

BACKGROUND ARTS

Many pyrethroid compounds are known and developed for pesticidal use. 5-Benzyl-3-furylmethyl 2,2-dimethyl-3-(2-cyano-3-ethoxy-3-oxo-1-propenyl)cyclopropanecarboxylate is disclosed in Pestic. Sci., 1976, 7, p. 499-502.

DISCLOSURE OF THE INVENTION

The present invention provides an ester compound of the following formula (1):

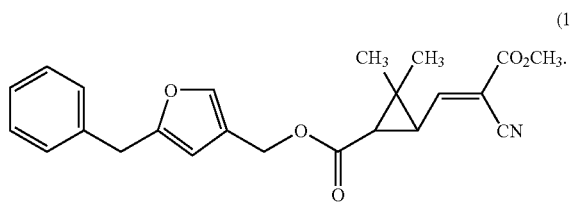

Namely, the present invention provides 5-benzyl-3-furylmethyl 2,2-dimethyl-3-((E)-2-cyano-3-methoxy-3-oxo-1-propenyl)cyclopropanecarboxylate shown by the formula (1) (hereinafter, referred to as "the present compound"), a pesticidal composition which comprises the present compound as an active ingredient and an inert carrier, and a method for controlling pests which comprises applying an effective amount of the present compound to the pests or locus where the pests inhabit.

MODE FOR CARRYING OUT THE INVENTION

The present compound has the isomers originated from two asymmetric carbon atoms on the cyclopropane ring and the isomers originated from the double bond. The present invention includes any active isomers and compounds containing the isomers at any ratio.

Embodiments of the present compound include, for example, the following compounds:

the ester compound of formula (1), wherein the absolute configuration of 1-position on the cyclopropane ring is R-configuration;

the ester compound of formula (1) wherein the relative configuration of the substituent on 1-position of the cyclopropane ring and the substituent on 3-position of the cyclopropane ring is trans configuration;

the ester compound of formula (1) wherein the absolute configuration of 1-position on the cyclopropane ring is R-configuration and the relative configuration of the substituent on 1-position of the cyclopropane ring and the substituent on 3-position of the cyclopropane ring is trans configuration;

the ester compound of formula (1) containing 80% or more of the isomer, which is the absolute configuration of 1-position on the cyclopropane ring is R-configuration;

the ester compound of formula (1) containing 80% or more of the isomer, which is the relative configuration of the substituent on 1-position of the cyclopropane ring and the substituent on 3-position of the cyclopropane ring is trans configuration;

the ester compound of formula (1) containing 80% or more of the isomer, which is the absolute configuration of 1-position on the cyclopropane ring is R-configuration and the relative configuration of the substituent on 1-position of the cyclopropane ring and the substituent on 3-position of the cyclopropane ring is trans configuration;

the ester compound of formula (1) containing 90% or more of the isomer, which is the absolute configuration of 1-position on the cyclopropane ring is R-configuration;

the ester compound of formula (1) containing 90% or more of the isomer, which is the relative configuration of the substituent on 1-position of the cyclopropane ring and the substituent on 3-position of the cyclopropane ring is trans configuration; and the ester compound of formula (1) containing 90% or more of the isomer, which is the absolute configuration of 1-position on the cyclopropane ring is R-configuration and the relative configuration of the substituent on 1-position of the cyclopropane ring and the substituent on 3-position of the cyclopropane ring is trans configuration.

The present compound can be produced, for example, by Production Process 1 and Production Process 2.

Production Process 1

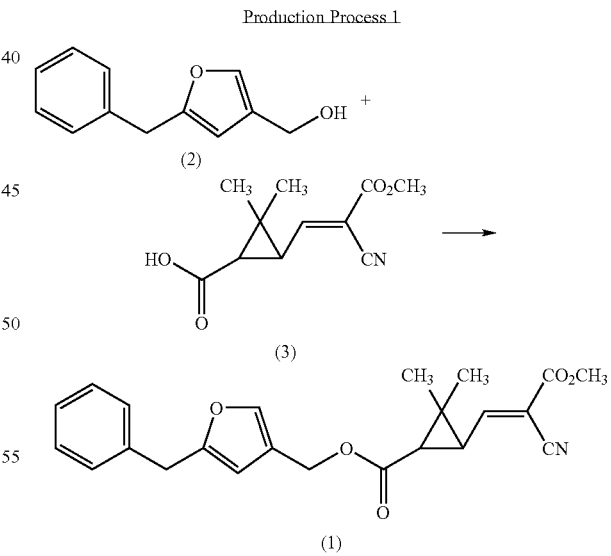

The present compound can be produced by making 5-benzyl-3-furylmethanol shown by the formula (2) (hereinafter, referred to as the compound (2)) react with 2,2-dimethyl-3-((E)-2-cyano-3-methoxy-3-oxo-1-propenyl)cyclopropanecarboxylic acid shown by the formula (3) (hereinafter, referred to as the compound (3)) in the presence of a condensing agent.

The reaction is usually carried out in a solvent. The solvent to be used in the reaction includes, for example, aliphatic hydrocarbons such as hexane, heptane, octane, nonane and the like; aromatic hydrocarbons such as toluene, xylene, mesitylene and the like; halogenated hydrocarbons such as 1,2-dichloroethane, chlorobenzene, dichlorobenzene, benzotrifluoride and the like; ethers such as diisopropyl ether, 1,4-dioxane, tetrahydrofuran, ethylene glycol dimethyl ether, diethylene glycol dimethyl ether and the like; acid amides such as N,N-dimethylformamide and the like; sulfoxides such as dimethyl sulfoxide, sulfolane and the like; and the mixture thereof.

The condensing agent to be used in the reaction includes, for example, carbodiimides such as dicyclohexylcarbodiimide, 1-ethyl-3-(3-dimethylaminopropyl)carbodiimide hydrochloride and the like.

Furthermore the reaction may be carried out in the presence of 4-(dimethylamino)pyridine.

The amount of the compound (3) is usually 0.7 to 1.5 moles, the amount of the condensing agent is usually 1 to 5 moles, relative to 1 mole of the compound (2). The amount of 4-(dimethylamino)pyridine is usually 0.01 to 1 mole, if necessary, relative to 1 mole of the compound (2).

The reaction temperature is usually in the range of 0 to 150° C., and the reaction time is usually in the range of 1 to 72 hours.

After completion of the reaction, the present compound can be isolated by subjecting the reaction mixture to ordinary post-treatment such as adding the reaction mixture into water, extracting with an organic solvent, and concentrating the organic layer. The isolated present compound can be purified by a technique such as chromatography and the like, if necessary.

The compound (2) was disclosed in U.S. Pat. No. 3,466,304, and can be produced by, for example, the method described in U.S. Pat. No. 3,466,304.

The compound (3) was disclosed in Japanese patent publication after examination S42-7906B, and can be produced by, for example, the following method.

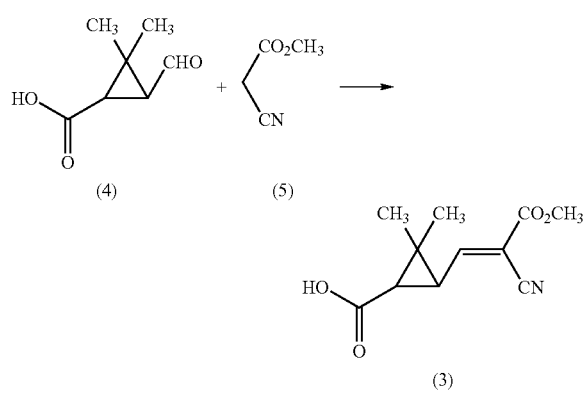

The compound (3) can be produced by making 2,2-dimethyl-3-formylcyclopropanecarboxylic acid shown by the formula (4) (hereinafter, referred to as the compound (4)) react with methyl 2-cyanoacetate shown by the formula (5) (hereinafter, referred to as the compound (5)) in a solvent.

The solvent to be used in the reaction includes, for example, aliphatic hydrocarbons such as hexane, heptane, octane, nonane and the like; aromatic hydrocarbons such as toluene, xylene, mesitylene and the like; halogenated hydrocarbons such as 1,2-dichloroethane, chlorobenzene, dichlorobenzene, benzotrifluoride and the like; ethers such as diisopropyl ether, 1,4-dioxane and the like; alcohols such as methanol, ethanol and the like; and the mixture thereof.

The reaction is usually carried out in the presence of a catalyst. The catalyst includes, for example, salts of organic acid such as ammonium acetate, sodium acetate and the like; organic bases such as piperidine, piperazine, morpholine, pyridine, triethylamine and the like.

The amount of the compound (5) is usually 1.0 to 1.5 mole, and the amount of the catalyst 0.05 to 1 mole, relative to 1 mole of the compound (4).

The reaction temperature is usually in the range of 50 to 150° C., and the reaction time is usually in the range of 0.5 to 10 hour.

Preferably, the reaction is carried out removing the water generated from the reaction under the condition of azeotropic dehydration.

After completion of the reaction, the compound (3) can be isolated by subjecting the reaction mixture to ordinary post-treatment such as adding the reaction mixture into water, extracting with an organic solvent, and concentrating the organic layer. The isolated compound (3) can be purified by a technique such as recrystallization and the like, if necessary.

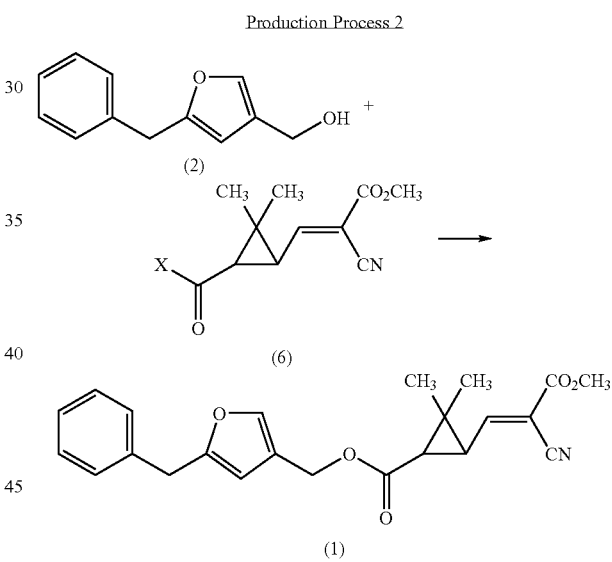

wherein X represents halogen atom such as chlorine atom and bromine atom.

The present compound can be produced by making the compound (2) react with 2,2-dimethyl-3-((E)-2-cyano-3-methoxy-3-oxo-1-propenyl)cyclopropanecarbonic acid halide shown by the formula (6) (hereinafter, referred to as the compound (6)).

The reaction usually carried out in a solvent in the presence of a base. The solvent to be used in the reaction includes, for example, aliphatic hydrocarbons such as hexane, heptane, octane, nonane and the like; aromatic hydrocarbons such as toluene, xylene, mesitylene and the like; halogenated hydrocarbons such as 1,2-dichloroethane, chlorobenzene, dichlorobenzene, benzotrifluoride and the like; ethers such as diisopropyl ether, 1,4-dioxane, tetrahydrofuran, ethylene glycol dimethyl ether, diethylene glycol dimethyl ether and the like; and the mixture thereof.

The base to be used in the reaction includes, for example, organic base such as triethylamine, pyridine, N,N-diethylaniline, 4-(dimethylamino)pyridine, diisopropylethylamine and the like.

The amount of the compound (6) is usually 0.7 to 1.5 mole, and the amount of the base is usually 1 to 5 moles, relative to 1 mole of the compound (2).

The reaction temperature is usually in the range of −20 to 100° C., and the reaction time is usually in the range of 1 to 72 hours.

After completion of the reaction, the present compound can be isolated by subjecting the reaction mixture to ordinary post-treatment such as adding the reaction mixture into water, extracting with an organic solvent, and concentrating the organic layer. The isolated present compound can be purified by a technique such as chromatography and the like, if necessary.

Examples of the pests controlled by the present compound include arthropods such as insects and acarina. Typical examples are as follows.

Lepidoptera:
Pyralidae such as *Chilo suppressalis* (rice stem borer), *Cnaphalocrocis medinalis* (rice leafroller) and *Plodia interpunctella* (Indian meal moth); Noctuidae such as *Spodoptera litura* (tobacco cutworm), *Pseudaletia separata* (rice armyworm) and *Mamestra brassicae* (cabbage armyworm); Pieridae such as *Pieris rapae crucivora* (common cabbageworm); Tortricidae such as *Adoxophyes* spp.; Carposinidae; Lyonetiidae; Lymantriidae; Plusiinae; *Agrotis* spp. such as *Agrotis segetum* (turnip cutworm) and *Agrotis ipsilon* (black cutworm); *Helicoverpa* spp.; *Heliotis* spp.; *Plutella xylostella* (diamondback moth); *Parnara guttata* (rice skipper); *Tinea transluens* (casemaking clothes moth); *Tineola bisselliella* (webbing clothes moth); and so on;

Diptera:
*Culex* spp. such as *Culex pipiens pallens* (common mosquito) and *Culex tritaeniorhynchus*; *Aedes* spp. such as *Aedes aegypti* (yellow fever mosquito) and *Aedes albopictus*; *Anopheles* spp. such as *Anopheles sinensis*; Chironomidae (midges); Muscidae such as *Musca domestica* (housefly), *Muscina stabulans* (false stablefly) and *Fannia canicularis* (little housefly); Calliphoridae; Sarcophagidae; Anthomyiidae such as *Delia platura* (seedcorn maggot) and *Delia antiqua* (onion maggot); Tephritidae (fruit flies); Drosophilidae; Psychodidae (moth flies); Phoridae; Tabanidae; Simuliidae (black flies); Stomoxyidae; Ceratopogonidae (biting midges); and so on;

Dictyoptera:
*Blattella germanica* (German cockroach), *Periplaneta fuliginosa* (smokybrown cockroach), *Periplaneta americana* (American cockroach), *Periplaneta brunnea* (brown cockroach), *Blatta orientalis* (oriental cockroach) and so on;

Hymenoptera:
Formicidae (ants); Vespidae (hornets); Bethylidae; Tenthredinidae (sawflies) such as *Athalia rosae ruficornis* (cabbage sawfly); and so on;

Siphonaptera:
*Ctenocephalides canis* (dog flea), *Ctenocephalides felis* (cat flea), *Pulex irritans* (human flea) and so on;

Anoplura:
*Pediculus humanus* (human body louse), *Pthirus pubis* (crab louse), *Pediculus capitis* (head louse), *Pediculus corporis* and so on;

Isoptera:
*Reticulitermes speratus; Coptotermes formosanus*; and so on;

Hemiptera:
Delphacidae (planthoppers) such as *Laodelphax striatellus* (small brown planthopper), *Nilaparvata lugens* (brown planthopper) and *Sogatella furcifere* (white-backed rice planthopper); leafhoppers such as *Nephotettix cincticeps, Nephotettix virescens*; Aphididae (aphids); Heteroptera (plant bugs); Aleyrodidae (whiteflies); scales; Tingidae (lace bugs); Psyllidae; and so on;

Coleoptera (Beetles):
*Attagenus unicolor japonicus* (black carpet beetle) and *Authrenus verbasci* (varied carpet beetle); corn rootworms such as *Diabrotica virgifera* (western corn rootworm) and *Diabrotica undecimpunctata howardi* (southern corn rootworm); Scarabaeidae such as *Anomala cuprea* (cupreous chafer) and *Anomala rufocuprea* (soybean beetle); Curculionidae (weevils) such as *Sitophilus zeamais* (maize weevil), *Lissorhoptrus oryzophilus* (ricewater weevil), ball weevil and *Callosohruchus chinensis* (adzuki bean weevil); Tenebrionidae (darkling beetles) such as *Tenebrio molitor* (yellow mealworm) and *Tribolium castaneum* (red flour beetle); Chrysomelidae (leaf beetles) such as *Oulema oryzae* (rice leaf beetle), *Phyllotreta striolata* (striped flea beetle) and *Aulacophora femoralis* (cucurbit leaf beetle); Anobiidae; *Epilachna* spp. such as *Epilachna vigintioctopunctata* (twenty-eight-spotted ladybird); Lyctidae (powderpost beetles); Bostrychidae (false powderpost beetles); Cerambycidae; *Paederus fuscipes* (robe beetle); and so on;

Thysanoptera:
*Thrips palmi, Flankliniella occidentalis* (western flower thrips), *Thrips hawaiiensis* (flower thrips) and so on;

Orthoptera:
Gryllotalpidae (mole crickets); Acrididae (grasshoppers); and so on;

Acarina:
Dermanyssidae such as *Dermatophagoides farinae* (American house dust mite) and *Dermatophagoides pteronyssinus*; Acaridae such as *Tyrophagus putrescentiae* (mold mite) and *Aleuroglyphus ovatus* (brown legged grain mite); Glycyphagidae such as *Glycyphagus privatus, Glycyphagus domesticus* and *Glycyphagus destructor* (groceries mite); Cheyletidae such as *Chelacaropsis malaccensis* and *Cheyletus fortis*; Tarsonemidae; *Chortoglyphus* spp.; *Haplochthonius* spp.; Tetranychidae such as *Tetranychus urticae* (two-spotted spider mite), *Tetranychus kanzawai* (Kanzawa spider mite), *Panonychus citri* (citrus red mite) and *Panonychus ulmi* (European red mite); Ixodidae such as *Haemaphysalis longiconis*; and so on.

The pesticidal composition of the present invention is comprised the present compound and an inert carrier, it is formulated in general process.

Examples of the formulations include oil solutions, emulsifiable concentrates, wettable powders, flowable formulations (e.g. aqueous suspension, aqueous emulsion), dusts, granules, aerosols, volatile formulations by heating (e.g. mosquito-coil, mosquito-mat for electric heater, liquid for electric heater), heating fumigants (e.g. combustible fumigant, chemical fumigant, porous ceramic fumigant), non-heating volatile formulations (e.g. resin volatile formulations, impregnated paper volatile formulations), smoking formulations (e.g. fogging), ULV formulations and poisonous bait.

The formulation methods are, for example, as follows.

(1) A method of mixing the present compound with a solid carrier, liquid carrier, gaseous carrier, bait or the like, optionally adding auxiliaries for formulation such as surfactants and the like, and formulating the mixture.

(2) A method of impregnating a base material containing no active ingredients with the present compound.

(3) A method of mixing the present compound with a base material and forming the mixture.

The content of the present compound in the pesticidal composition of the present invention depends on the type of formulations, but these formulations usually contain 0.001 to 95% by weight of the present compound.

Examples of the carrier to be used for the formulation include solid carriers such as clays (e.g. kaolin clay, diatomaceous earth, synthetic hydrated silicon oxide, bentonite, Fubasami clay, acid clay), talc and the like, ceramics, other inorganic minerals (e.g. sericite, quartz, sulfur, active carbon, calcium carbonate, hydrated silicon oxide, montmorillonite) and chemical fertilizers (e.g. ammonium sulfate, ammonium phosphate, ammonium nitrate, urea, ammonium chloride); liquid carriers such as water, alcohols (e.g. methanol, ethanol), ketones (e.g. acetone, methyl ethyl ketone), aromatic hydrocarbons (e.g. benzene, toluene, xylene, ethylbenzene, methylnaphthalene, phenylxylylethane), aliphatic hydrocarbons (e.g. hexane, cyclohexane, kerosene, gas oil), esters (ethyl acetate, butyl acetate), nitriles (e.g. acetonitrile, isobutyronitrile), ethers (e.g. diisopropyl ether, dioxane), acid amides (e.g. N,N-dimethylformamide, N,N-dimethylacetamide), halogenated hydrocarbons (dichloromethane, trichloroethane, carbon tetrachloride), dimethyl sulfoxide, vegetable oils (e.g. soybean oil, cottonseed oil); and gaseous carriers such as flon gas, butane gas, LPG (liquefied petroleum gas), dimethyl ether and carbon dioxide.

Examples of the surfactant include alkyl sulfates, alkylsulfonate salts, alkylarylsulfonate salts, alkyl aryl ethers, polyoxyethylenealkyl aryl ethers, polyethylene glycol ethers, polyhydric alcohol esters and sugar alcohol derivatives.

Examples of the other auxiliaries for formulation include sticking agents, dispersing agents and stabilizers, typically casein, gelatin, polysaccharides (e.g. starch, gum arabic, cellulose derivatives, alginic acid), lignin derivatives, bentonite and synthetic water-soluble polymers (e.g. polyvinyl alcohol, polyvinyl pyrrolidone), polyacrylic acid, BHT (2,6-di-tert butyl-4-methylphenol) and BHA (mixture of 2-tert-butyl-4-methoxyphenol and 3-tert-butyl-4-methoxyphenol).

The base material of the mosquito-coil is, for example, a mixture of raw plant powder such as wood powder and Pyrethrum marc and a binding agent like Tabu powder (powder of *Machilus thunbergii*), starch or gluten.

The base material of the mosquito-mat for electric heating is, for example, a plate of compacted fibrils of cotton linters or a mixture of pulp and cotton linters.

The base material of the combustible fumigant includes, for example, exothermic agents (e.g. nitrates, nitrites, guanidine salts, potassium chlorate, nitrocellulose, ethylcellulose, wood powder), pyrolytic stimulating agents (e.g. alkali metal salts, alkaline earth metal salts, dichromates and chromates), oxygen sources (e.g. potassium nitrate), combustion assistants (e.g. melanin, wheat starch), bulk fillers (e.g. diatomaceous earth) and binding agents (e.g. synthetic glue).

The base material of the chemical fumigant includes, for example, an exothermic agents (e.g. alkali metal sulfides, polysulfides, hydrogensulfides, calcium oxide), catalytic agents (e.g. carbonaceous substances, iron carbide and activated clay), organic foaming agents (e.g. azodicarbonamide, benzenesulfonylhydrazide, dinitrosopentamethylene tetramine, polystyrene, polyurethane) and fillers (e.g. natural or synthetic fibers).

The base material of the non-heating volatile formulation, for example include thermoplastic resins and paper (e.g. filter paper, Japanese paper).

The base material of the poisonous bait includes bait components (e.g. grain powder, vegetable oil, sugar, crystalline cellulose), antioxidants (e.g. dibutylhydroxytoluene, nordihydroguaiaretic acid), preservatives (e.g. dehydroacetic acid), substances for preventing erroneous eating from children and pets (e.g. red pepper powder), pest-attractant flavors (e.g. cheese flavor, onion flavor, peanut oil).

The method for controlling pests of the present invention is usually carried out by applying the pesticidal composition of the present invention to the pests or locus where the pests inhabit.

The application methods of the pesticidal composition of the present invention are, for example, given below. The methods are suitably selected according to the type of the pesticidal composition or application places.

(1) A method applying the pesticidal composition of the present invention as it is to pests or locus where the pests inhabit.

(2) A method diluting the pesticidal composition of the present invention with a solvent such as water, and then applying it to pests or locus where the pests inhabit.

In that case, the pesticidal composition of the present invention formulated to emulsifiable concentrates, wettable powders, flowable formulations, microcapsule formulations and so on is diluted to make the concentration of the present compound to 0.1 to 10000 ppm.

(3) A method volatilizing an active ingredient by heating or at ordinary temperature the pesticidal composition of the present invention at a place where pests inhabit.

In those cases, the dosage of the present compound is decided according to type of the pesticidal composition of the present invention, time, place and method of the application, kind of the pests, damage and so on. But the dosage of the present compound is usually 1 to 10000 $mg/m^2$ for planer application or 0.1 to 5000 $mg/m^3$ for spatial application.

The pesticidal composition of the present invention can be used simultaneously with the other insecticide, nematocide, soil-pest controlling agent, fungicide, herbicide, plant growth regulator, repellent, synergist, fertilizer or soil conditioner under pre-mixed conditions or non-mixed conditions.

Examples of the active ingredients of the insecticide and acaricide include organophosphorus compounds such as fenitrothion, fenthion, diazinon, chlorpyrifos, acephate, methidathion, disulfoton, DDVP, sulprofos, cyanophos, dioxabenzofos, dimethoate, phenthoate, malathion, trichlorfon, azinphos-methyl, monocrotophos and ethion; carbamate compounds such as BPMC, benfracarb, propoxur, carbosulfan, carbaryl, methomyl, ethiofencarb, aldicarb, oxamyl and fenothiocarb; pyrethroid compounds such as etofenprox, fenvalerate, esfenvalerate, fenpropathrin, cypermethrin, permethrin, cyhalothrin, deltamethrin, cycloprothrin, fluvalinate, bifenthrin, 2-methyl-2-(4-bromodifluoromethoxyphenyl)propyl 3-phenoxybenzyl ether, tralomethrin, silafluofen, d-phenothrin, cyphenothrin, d-resmethrin, acrinathrin, cyfluthrin, tefluthrin, transfluthrin, tetramethrin, allethrin, prallethrin, empenthrin, imiprothrin, d-furamethrin and 5-(2-propynyl)furfuryl 2,2,3,3-tetramethylcyclopropanecarboxylate; nitroimidazolidine derivatives;

N-cyanoamidine derivatives such as acetamiprid; chlorinated hydrocarbons such as endosulfan, γ-BHC and 1,1-bis(chlorophenyl)-2,2,2-trichloroethanol; benzoylphenylurea compounds such as chlorfluazuron, teflubenzuron and flufenoxuron; phenylpyrazole compounds; metoxadiazon; bromopropylate; tetradifon; chinomethionat; pyridaben; fenpyroximate; diafenthiuron; tebufenpyrad; polynactins complex such as tetranactin, dinactin and trinactin; pyrimidifen; milbemectin; abamectin; ivermectin; and azadirachtin.

Examples of active ingredient of the repellent include 3,4-caranediol, N,N-diethyl-m-toluamide, 1-methylpropyl 2-(2-hydroxyethyl)-1-piperidinecarboxylate, p-menthane-3,8-diol, botanical essential oils (e.g. hyssop oil).

Examples of active ingredient of the synergist include bis (2,3,3,3-tetrachloropropyl) ether (S-421), N-(2-ethylhexyl) bicyclo[2.2.1]hept-5-ene-2,3-dicarboximide (MGK-264) and 5-[2-(2-butoxyethoxy)ethoxymethyl]-6-propyl-1,3-benzodioxole (piperonyl butoxide).

EXAMPLES

The present invention is explained by production example, formulation examples, test example and so on, and the present invention is not restricted by these examples.

At first, the production example of the present compound is given below.

Production Example

In 50 ml round bottom flask were added 0.67 g of 5-benzyl-3-furylmethanol, 0.79 g of 1R-trans-2,2-dimethyl-3-((E)-2-cyano-3-methoxy-3-oxo-1-propenyl)cyclopropanecarboxylic acid, 0.13 g of 4-(dimethylamino)pyridine and 10 ml of methylene chloride, and 0.80 g of dicyclohexylcarbodiimide was added at room temperature. The mixture was stirred at room temperature for 3 hours. The reaction mixture was subjected to suction filtration with glass filter, and the residue was washed with 40 ml of diethyl ether. The filtrate were combined, and concentrated under reduced pressure. The obtained crude oily product was subjected to silica gel column chromatography to obtain 0.59 g of 5-benzyl-3-furylmethyl 1R-trans-2,2-dimethyl-3-((E)-2-cyano-3-methoxy-3-oxo-1-propenyl)cyclopropan ecarboxylate (hereinafter, referred to as the present compound (1)) in 42% yield.

$^1$H-NMR (CDCl$_3$, TMS) δ (ppm): 1.30 (s, 3H), 1.32 (s, 3H), 2.10 (d, 1H), 2.64 (dd, 1H), 3.84 (s, 3H), 3.93 (s, 2H), 4.94 (q, 2H), 6.04 (s, 1H), 7.21-7.39 (m, 7H)

Formulation examples are given below. Part(s) means part(s) by weight.

Formulation Example 1

Twenty parts of the present compound (1) are dissolved in 65 parts of xylene. Fifteen parts of Sorpol 3005X (registered trademark of Toho Chemical) are added thereto, stirred and mixed well to give emulsifiable concentrate.

Formulation Example 2

Five parts of Sorpol 3005X are added to 40 parts of the present compound (1) and mixed well. Thirty-two parts of Carplex #80 (synthetic hydrated silica, registered trademark of Shionogi & Co.) and 23 parts of 300-mesh distomaceous earth are added thereto and mixed well with a juice mixer to give wettable powder.

Formulation Example 3

A mixture of 10 parts of the present compound (1), 10 parts of phenylxylylethane and 0.5 part of Sumidur L-75 (tolylene-diisocyanate manufactured by Sumika Bayer Urethane Co., Ltd.) is added to 20 parts of a 10% aqueous solution of gum arabic, and stirred with a homomixer to give an emulsion having the mean particle diameter of 20 μm. Two parts of ethylene glycol are added thereto and stirred 24 hours on a water bath of 60° C. to give a microcapsule slurry. A thickening agent solution is prepared by dispersing 0.2 part of xanthan gum and 1.0 part of Beagum R (aluminum magnesium silicate manufactured by Sanyo Chemical Co., Ltd.) in 56.3 parts of ion-exchanged water. Forty-two and a half (42.5) parts of the above microcapsule slurry and 57.5 parts of the above thickening agent solution are mixed to give microencapsulated formulation.

Formulation Example 4

A mixture of 10 parts of the present compound (1) and 10 parts of phenylxylylethane is added to 20 parts of a 10% aqueous solution of polyethylene glycol and stirred with a homomixer to give an emulsion having the mean particle diameter of 3 μm. A thickening agent solution is prepared by dispersing 0.2 part of xanthan gum and 1.0 part of Beagum R (aluminum magnesium silicate manufactured by Sanyo Chemical Co., Ltd.) in 58.8 parts of ion-exchanged water. Forty parts of the above emulsion and 60 parts of the above thickening agent solution are mixed to give flowable formulation.

Formulation Example 5

Five parts of the present compound (1) are mixed with 3 parts of Carplex #80 (fine powder of synthetic hydrated silicon dioxide, trademark of Shionogi & Co.), 0.3 parts of PAP (mixture of monoisopropyl phosphate and diisopropyl phosphate) and 91.7 parts of 300-mesh talc, and stirred with a juice mixer to give dust.

Formulation Example 6

One-tenth (0.1) part of the present compound (1) is dissolved in 5 parts of dichloromethane and mixed with 94.9 parts of deodorized kerosene to give oil solution.

Formulation Example 7

An aerosol vessel is filled with the solution obtained by dissolving 1 part of the present compound (1) with 5 parts of dichloromethane and 34 parts of deodorized kerosene. The vessel is then equipped with a valve and 60 parts of propellant (liquefied petroleum gas) are charged through the valve into the aerosol vessel under pressure to give oil-based aerosol.

Formulation Example 8

An aerosol vessel is filled with 50 parts of water and a mixture of 0.6 part of the present compound (1), 5 parts of xylene, 3.4 parts of deodorized kerosene and 1 part of Atmos 300 (emulsifier, trademark of Atlas Chemical Co.). The vessel is then equipped with a valve and 40 parts of propellant (liquefied petroleum gas) is charged through the valve into the aerosol vessel under pressure to give water-based aerosol.

Formulation Example 9

A solution prepared by dissolving 0.3 g of the present compound (1) in 20 ml of acetone is homogeneously mixed with 99.7 g of a carrier for a mosquito-coil (mixture of Tabu powder, Pyrethrum marc and wood powder at the ratio of 4:3:3). After 100 ml of water is added, the mixture is kneaded well, molded and dried to give mosquito-coil.

Formulation Example 10

Ten milliliters (10 ml) of solution is prepared by dissolving 0.8 g of the present compound (1) and 0.4 g of piperonyl butoxide in acetone. 0.5 ml of the obtained solution is impregnated with a base material (a plate of compacted fibrils of a mixture of pulp and cotton linter: 2.5 cm×1.5 cm×0.3 cm of thickness) homogeneously to give mosquito-mat.

Formulation Example 11

Three parts of the present compound (1) is dissolved in 97 parts of deodorized kerosene. The obtained solution is charged in a vessel of polyvinyl chloride. In the vessel is inserted a porous absorptive wick which is inorganic powder solidified with a binder and then calcined, the upper portion of which wick can be heated with a heater, to give a part of an electric heating fumigation device.

Formulation Example 12

A solution prepared by dissolving 100 mg of the present compound (1) in an appropriate amount of acetone is impregnated with a porous ceramic plate (4.0 cm×4.0 cm×1.2 cm of thickness) to give fumigant for heating.

Formulation Example 13

A solution prepared by dissolving 100 µg of the present compound (1) in an appropriate amount of acetone is applied onto filter paper (2.0 cm×2.0 cm×0.3 mm of thickness) and the acetone is vaporized to give volatile agent for using at room temperature.

Formulation Example 14

A acetone solution of the present compound (1) is impregnated with a filter paper, so that the amount of the present compound is 1 g per 1 m² and the acetone is vaporized, to give a sheer for controlling mite.

The following test example shows that present compound is useful as an active ingredient of a pesticidal composition.

Test Example 1

A solution of 0.025 part of the present compound (1) dissolved with 10 parts of dichloromethane was mixed with 89.975 parts of deodorized kerosene to give a 0.025% oil solution.

Ten female common mosquitoes (*Culex pipiens pallens*) were left in a cubic chamber (70 cm at side). Seven-tenths (0.7) ml of the 0.025% oil solution of the present compound (1) was sprayed with a spray gun at a pressure of $8.8 \times 10^4$ Pa from a small window on the side of the chamber. Then, the number of the knocked-down insects was counted at times for 10 minutes. The time ($KT_{50}$) for knocking down half of the tested insects was calculated from the result.

For the comparison, 5-benzyl-3-furylmethyl 1R-trans-2,2-dimethyl-3-((E)-2-cyano-3-ethoxy-3-oxo-1-propenyl)cyclopropanecarboxylate (hereinafter, referred to as the comparison compound) was also subjected to the above mentioned test. The test was done twice for one compound. The results are shown in Table 1.

TABLE 1

|  | KT50 (minute) |
| --- | --- |
| The present compound (1) | 0.7 |
| The comparison compound | 6.1 |

INDUSTRIAL APPLICABILITY

The present compound can effectively control pests such as insect pest and the like.

The invention claimed is:

1. An ester compound given by the formula (1):

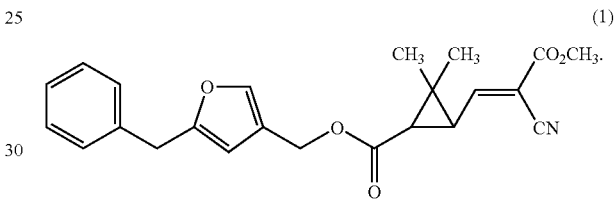

2. The ester compound according to claim 1, wherein the substituent on 1-position of the cyclopropane ring is in trans configuration relative to the substituent on 3-position of the cyclopropane ring.

3. An acarina-controlling composition comprising the ester compound described in claim 1 as an active ingredient and an inert carrier.

4. A method for controlling acarina comprising applying an effective amount of the ester compound described in claim 1 to the acarina or locus where the acarina inhabit.

5. An insect-controlling composition comprising the ester compound described in claim 1 as an active ingredient and an inert carrier.

6. A method for controlling insects comprising applying an effective amount of the ester compound described in claim 1 to the insects or locus where the insects inhabit.

7. The insect-controlling composition of claim 5, wherein the composition is effective in controlling insects selected from the group consisting of Lepidoptera, Diptera, Dictyoptera, Hymenoptera, Siphonaptera, Anoplura, Isoptera, Hemiptera, Coleoptera, Thysanoptera and Orthoptera.

8. The method of claim 6, wherein the insects are selected from the group consisting of Lepidoptera, Diptera, Dictyoptera, Hymenoptera, Siphonaptera, Anoplura, Isoptera, Hemiptera, Coleoptera, Thysanoptera and Orthoptera.

* * * * *